United States Patent [19]

Erckel et al.

[11] 4,282,355
[45] Aug. 4, 1981

[54] PROCESS FOR THE MANUFACTURE OF BIS-BENZOXAZOLYL-STILBENE COMPOUNDS

[75] Inventors: Rüdiger Erckel; Peter Jürges, both of Eppstein, Fed. Rep. of Germany

[73] Assignee: Hoechst Aktiengesellschaft, Fed. Rep. of Germany

[21] Appl. No.: 121,296

[22] Filed: Feb. 14, 1980

[51] Int. Cl.$^3$ .................................... C07D 413/10
[52] U.S. Cl. .................................... 542/459; 548/217
[58] Field of Search .................... 542/459; 548/217

[56] References Cited

U.S. PATENT DOCUMENTS

| | | | |
|---|---|---|---|
| 3,455,837 | 7/1969 | Maeder et al. | 542/459 |
| 3,786,064 | 1/1974 | Harnisch | 548/217 |
| 3,850,914 | 11/1974 | Luthi | 542/459 |
| 3,860,584 | 1/1975 | Meyer | 542/459 |
| 3,926,963 | 12/1975 | Meyer | 542/459 |
| 3,926,964 | 12/1975 | Liechtl | 542/459 |

OTHER PUBLICATIONS

Weiss et al., J. Am. Chem. Soc. 80(1958) pp. 4657–4658.

*Primary Examiner*—Arthur P. Demers
*Attorney, Agent, or Firm*—Connolly and Hutz

[57] ABSTRACT

Process for the manufacture of bis-benzoxazolyl-stilbene compounds which comprises the chlorination in an inert organic solvent of benzoxazolyl-stilbene carboxylic acid, addition of a solution of an aminophenol in an aprotic, dipolar solvent to the acid chloride thus obtained and subsequent cyclization in the presence of an acid catalyst of the acyl compound obtained.

1 Claim, No Drawings

PROCESS FOR THE MANUFACTURE OF BIS-BENZOXAZOLYL-STILBENE COMPOUNDS

Bis-benzoxazolyl-stilbenes have gained technical importance as optical brighteners, for example as spin brighteners or as so-components in optical brighteners for textile materials.

Up to now, they have been prepared, for example as described in U.S. Pat. No. 3,586,673, by reacting 4-benzoxazolyl-2,4'-stilbene-carboxylic acid in 1,2,4-trichlorobenzene with phosphorus oxychloride to give the acid chloride, subsequently adding a solid aminophenol and heating the reaction mixture. For purification the crude products obtained in this manner must be recrystallized repeatedly. A similar process is described in JA-PS No. 23,028/69.

One-stage processes for the manufacture of the above compounds have been described in DE-OS No. 2,247,791, method A, pages 16–17 and in DE-OS No. 2,315,955, Example 5. In both cases the acid chloride is reacted with aminophenol in trichlorobenzene and the amine formed is subjected to cyclization in the reaction mixture without previous isolation. In DE-OS No. 2,315,955 the aminophenol is dissolved in pyridine and the acid chloride is added in the form of a solution in trichlorobenzene. During the course of the reaction the pyridine distils off. In the process of DE-OS No. 2,247,791 the aminophenol is added in the form of a hot solution in trichlorobenzene. The processes yield products that are highly contaminated and that must be purified by recrystallization.

It has now been found, surprisingly, that bis-benzoxazolyl-stilbenes of the formula defined below can be obtained in a high purity in a one-stage process if a solution of aminophenol in an aprotic, dipolar solvent is added to the solution of a benzoxazolyl-stilbene-carboxylic acid in an inert solvent. In this manner products are obtained which can be directly used as optical brighteners without previous purification by recrystallization.

It is an objective of the present invention to provide a simple and economical process for the manufacture of bis-benzoxazolyl-stilbene compounds according to which the desired products are obtained in a high purity and in a good yield. According to the invention this objective is obtained by adding the aminophenol not in solid form but in the form of a solution in an aprotic, dipolar solvent.

It is, therefore, the object of the present invention to provide a process for the manufacture of bis-benzoxazolyl-stilbene compounds of the formula I

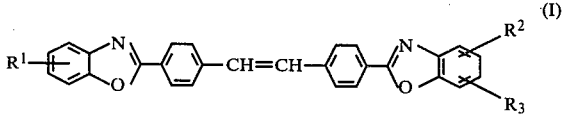

in which $R^1$, $R^2$ and $R^3$, independent of one another, denote hydrogen, $C_1$–$C_9$ alkyl, carbo-$C_1$–$C_4$ alkoxy and trifluoromethyl, at least two of the radicals $R^1$, $R^2$ and $R^3$ being hydrogen, by chlorination of an acid of the formula II

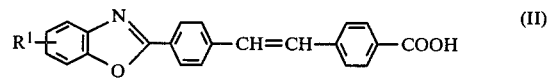

in which $R^1$ is as defined under formula I, in an inert organic solvent and subsequent reaction with an aminophenol of the formula III

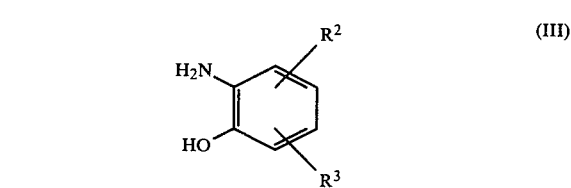

in which $R^2$ and $R^3$ are as defined under formula I, which comprises adding the aminophenol in the form of a solution in an aprotic, dipolar solvent, preparing the compound of the formula IV

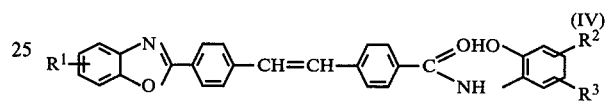

in which $R^1$, $R^2$ and $R^3$ are as defined under formula I by acylation and preparing therefrom the compound of the formula I by cyclization after addition of an acid catalyst.

To carry out the process of the invention the compound of the formula II is reacted in an inert organic solvent, for example o-dichlorobenzene, trichlorobenzene, tetrahydronaphthalene, optionally with the addition of a catalyst, for example a small amount of dimethyl formamide, with a chlorination agent such as thionyl chloride to give the acid chloride. The excess amount of chlorination agent is subsequently distilled off up to an internal temperature of 140° to 160° C., a complete removal possibly being promoted by passing an $N_2$ current over the reaction mixture. To this mixture, which is either a solution of a suspension, a solution of a compound of the formula III in an aprotic, dipolar solvent is then added dropwise at a temperature of from 100° to 200° C., preferably 150° to 160° C. and stirring is continued at 100° to 200° C., preferably 130° to 160° C. until the conversion into the compound of the formula IV is complete, which can be perceived by the termination of the hydrogen chloride generation.

Suitable aprotic solvents are N,N-dialkyl-carboxylic acid amides, for example dimethyl formamide, N-methylpyrrolidone, or hexamethyl-phosphoric acid trisamide, preferably, however, N-methylpyrrolidone. The aprotic, dipolar solvent (solvent B) is used in an amount of from 3 to 30 and preferably 5 to 15% by volume, calculated on the amount of inert organic solvent (solvent A) used for the reaction of the compound of the formula II. As mentioned above, suitable inert organic solvents are, for example, tetrahydronaphthalene, decahydronaphthalene or methylnaphthalene, the boiling point of which should not be below the reaction temperature.

The cyclization of compound IV to give compound I is carried out without intermediate isolation by heating the reaction mixture to a temperature of from 150° to 250° C., preferably the boiling point of solvent A and optionally in the presence of an acid catalyst. Suitable catalysts are, for example, boric acid, zinc chloride, p-toluenesulfonic acid and polyphosphoric acids, which are preferably used in an amount of from 0.5 to 5%, calculated on the amount of from 0.5 to 5%, calculated on the amount of compound II used.

When the cyclization is terminated, which can be perceived by the termination of the water separation, the reaction product is isolated in usual manner, for example by suction filtration after cooling to room temperature. Prior to filtration a low molecular weight alcohol, for example methanol or ethanol, may be added to the reaction mixture.

The compounds of the formula IV used as starting components are known from literature and can be produced by processes described in literature (cf. JA-PS No. 40,581/65, JA-PS No. 44-6979, JA-PS No. 7045/68, DE-OS No. 2,306,050, DE-OS No. 1,594,829 and DE-OS No. 2,129,818).

Preferred compounds to be produced by the process described above are compounds of the formula I a

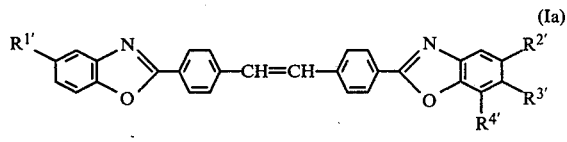
(Ia)

in which $R^{1'}$, $R^{2'}$, $R^{3'}$ and $R^{4'}$, independent of one another, denote hydrogen or $C_1$–$C_4$ alkyl and at least one of the radicals $R^{1'}$ to $R^{4'}$ is hydrogen.

In the process according to the invention the compounds of the formula I are obtained in an excellent purity and in an almost quantitative yield. Normally, no further purification by recrystallization is necessary. This is an especially important feature of bis-benzoxazolyl-stilbenes of the formula I generally have a poor solubility and, therefore, large amounts of solvent would be required for recrystallization. As compared therewith, all known processes, in which the aminophenol is not added in the form of a solution in an aprotic, dipolar solvent, yield dark yellow or brown products which possess a distinctly lesser brightening effect and, therefore, have to be redissolved.

The following examples illustrate the invention, the parts are by weight unless otherwise stated and the melting points are not corrected.

EXAMPLE 1

177 Parts of thionyl chloride are added over a period of approximately 1 hour to a suspension of 170 parts of 4(2-benzoxazolyl-2-4'-stilbene-carboxylic acid in 1150 parts of tetrahydronaphthalene, which suspension contains 5 parts of dimethyl formamide. The reaction mixture is heated to 110° C. within a period of about 2 hours and stirring at that temperature is continued for 1 hour. Next, the thionyl chloride in excess is distilled off in a nitrogen current down to an internal temperature of 150° C. At said temperature a solution of 65 parts of 2-amino-4-methylphenol in 125 parts of N-methylpyrrolidone is added dropwise and the reaction mixture is slowly heated to 170° C. within 3 hours. After addition of 5 parts of p-toluene-sulfonic acid, the mixture is heated to reflux temperature and the reaction water is separated over a water separator. When the water separation is terminated, the reaction mixture is cooled to 100° C., 320 parts of methanol are added dropwise and the mixture is refluxed for another hour. After cooling to room temperature, the mixture is filtered with suction and the residue is washed with methanol. After drying, 206 g (96% of theory) of the compound

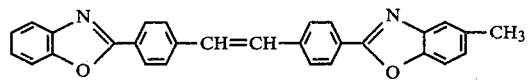

are obtained in the form of a light yellow powder having the following melting properties:
the product sinters at 266° to 270° C., it has a liquid-crystalline transition at 316° to 321° C. and it melts above 370° C. The tinctorial properties can be improved slightly only by repeated recrystallization from N-methylpyrrolidone with clarification with active carbon.

EXAMPLE 2

The reaction is carried out as defined in Example 1 with the exception that 5 part of phosphorus pentoxide are used instead of p-toluenesulfonic acid. The same compound is obtained in the same quality but in a slightly smaller yield.

EXAMPLE 3

The reaction is carried out as described in Example 1 with the exception that 1,2,4-trichlorovenzene is used as solvent instead of tetuenesulfonic acid. The same compound is obtained in an equally good quantity of a yield of 92% of the theory.

EXAMPLE 4

In the manner described in Examples 1 to 3 further optical brighteners of the formula Ia as specified in the following table can be prepared.

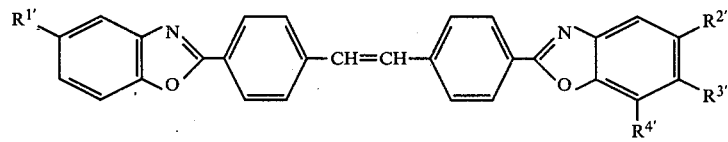

| Ex.No. | $R^{1'}$ | $R^{2'}$ | $R^{3'}$ | $R^{4'}$ | yield % of the theory | melting properties (°C.) sintering | liquid-crystalline | limpid | UV-absorption (measured in DMF) max (n m) | ($\times 10^{-4}$) | fluorescence (measured in DMF) max (n m) | Q |
|---|---|---|---|---|---|---|---|---|---|---|---|---|
| 4 | H | H | H | H | 94 | 318 | 323–330 | 340 | 374 | 8.36 | 432 | 0.82 |
| 5 | H | $CH_3$ | H | $CH_3$ | 91 | 265 | 266–267 | 278 | 376 | 8.61 | 435 | 0.92 |
| 6 | $CH_3$ | $CH_3$ | H | H | 92 | 268 | 312–315 | 338 | 377 | — | 436 | — |
| 7 | $CH_3$ | $CH_3$ | H | $CH_3$ | 86 | 241 | 248–256 | 269 | — | — | — | — |
| 8 | H | $iC_9H_{19}$ | H | H | 84 | | 251–254 | 277 | 377 | 8.85 | 435 | 0.85 |

-continued

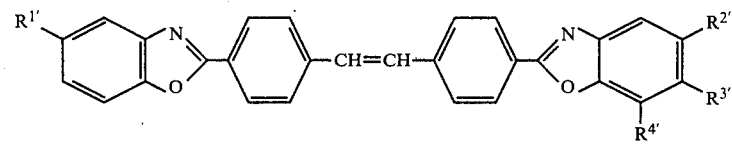

| Ex.No. | $R^{1'}$ | $R^{2'}$ | $R^{3'}$ | $R^{4'}$ | yield % of the theory | melting properties (°C.) sintering | liquid-crystalline | limpid | UV-absorption (measured in DMF) max (n m) | $(\times 10^{-4})$ | fluorescence (measured in DMF) max (n m) | Q |
|---|---|---|---|---|---|---|---|---|---|---|---|---|
| 9 | H | $CH_3$ | $CH_3$ | H | 89 | 298 | 304–321 | 325 | 378 | 9.04 | 439 | 0.90 |
| 10 | $CH_3$ | $CH_3$ | $CH_3$ | H | 83 | 296 | 321–330 | 333 | 380 | 8.84 | 441 | 0.91 |
| 11 | H | $COOCH_3$ | H | H | 95 | 260 | 298–314 | 336 | 374 | 8.24 | 434 | 0.85 |

What is claimed is:

1. Process for the manufacture of bis-benzoyloxazolyl-stilbene compounds of the formula I

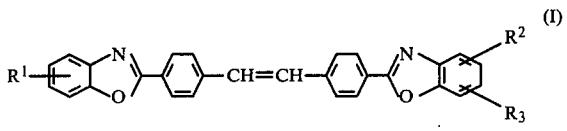

in which $R^1$, $R^2$ and $R^3$, independent of one another, denote hydrogen, $C_1$–$C_9$ alkyl, carbo-$C_1$–$C_4$ alkoxy and trifluoromethyl, at least two of the radicals $R^1$, $R^2$ and $R^3$ being hydrogen, by chlorination of an acid of the formula II

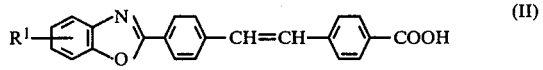

in which $R^1$ is as defined under formula I, in an inert organic solvent and subsequent reaction with an aminophenol of the formula III

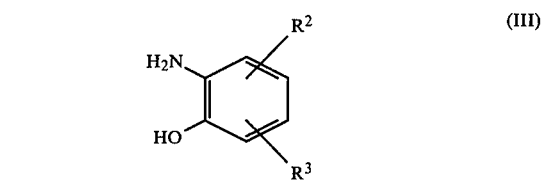

in which $R^2$ and $R^3$ are as defined under formula I, which comprises adding the aminophenol in the form of a solution in an aprotic, dipolar solvent, preparing the compound of the formula IV

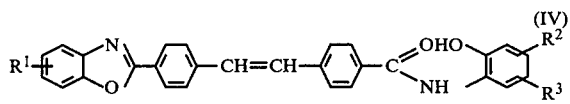

in which $R^1$, $R^2$ and $R^3$ are as defined under formula I by acylation and preparing therefrom the compound of the formula I by cyclization after addition of an acid catalyst.

* * * * *